United States Patent
Bernardoni et al.

(10) Patent No.: US 10,485,720 B2
(45) Date of Patent: Nov. 26, 2019

(54) APPARATUS FOR POSITIONING THE LOWER LIMB OF A PATIENT DURING OPERATION, IN PARTICULAR FOR HIP REPLACEMENT OPERATIONS WITH ANTERIOR APPROACH, AND SURGICAL POSITIONING SYSTEM COMPRISING SAID APPARATUS

(71) Applicant: MEDACTA INTERNATIONAL S.A., Castel San Pietro (CH)

(72) Inventors: Massimiliano Bernardoni, Figino (CH); Mirko Giardiello, Castel San Pietro (CH); Alberto Siccardi, Sonvico (CH); Francesco Siccardi, Sonvico (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 394 days.

(21) Appl. No.: 14/428,682

(22) PCT Filed: Sep. 17, 2013

(86) PCT No.: PCT/IB2013/058616
§ 371 (c)(1),
(2) Date: Mar. 17, 2015

(87) PCT Pub. No.: WO2014/045199
PCT Pub. Date: Mar. 27, 2014

(65) Prior Publication Data
US 2015/0231013 A1 Aug. 20, 2015

(30) Foreign Application Priority Data
Sep. 18, 2012 (IT) .............................. MI2012A1548

(51) Int. Cl.
*A61F 5/37* (2006.01)
*A61G 13/00* (2006.01)
*A61G 13/12* (2006.01)

(52) U.S. Cl.
CPC ........ *A61G 13/0036* (2013.01); *A61F 5/3769* (2013.01); *A61G 13/123* (2013.01);
(Continued)

(58) Field of Classification Search
CPC ........ A61F 5/37; A61F 5/3761; A61F 5/3769; A61F 5/3792; A61G 13/10; A61G 13/12;
(Continued)

(56) References Cited

U.S. PATENT DOCUMENTS 1,188,711 A * 6/1916 Wilting .............. A61G 13/0036
602/36
3,745,996 A 7/1973 Rush, Sr.
(Continued)

FOREIGN PATENT DOCUMENTS

DE 202012101347 U1 * 6/2012 ........... A61B 5/6829
FR 2632184 A1 12/1989
(Continued)

*Primary Examiner* — Keri J Nelson
*Assistant Examiner* — Adam Baker
(74) *Attorney, Agent, or Firm* — Allen, Dyer, Doppelt, + Gilchrist, P.A.

(57) ABSTRACT

Apparatus (20') for positioning the lower limb of a patient (500) during operation, in particular for hip replacement operations with anterior approach, comprising: a traction arm (30') with at least a distal portion (34', 36') defining a traction axis (x'); a support framework (40') coupled to said traction arm (30') so as to allow the adjustment of the position of one of its distal ends (32'); a coupling (60') constrained to said traction arm (30') and arranged to be associated to the distal end of the lower limb of the patient (500); at least a first actuator (34') which defines with its (Continued)

action a relative movement of the coupling (60') with respect to the traction arm (30'), at least a component of said relative movement being parallel to the traction axis (x').

8 Claims, 12 Drawing Sheets

(52) U.S. Cl.
CPC ......... *A61G 13/125* (2013.01); *A61G 13/128* (2013.01); *A61G 13/1225* (2013.01); *A61G 2200/58* (2013.01); *A61G 2210/50* (2013.01)

(58) Field of Classification Search
CPC ............ A61G 13/1235; A61G 13/1245; A61G 13/1255; A61G 13/1285; A61G 13/128; A61G 13/129; A61G 13/101; A61G 13/1205–1255; A61G 13/0036; A61G 13/0063; A61G 2200/32; A61G 7/065; A61G 7/075; A61G 7/0755; A61G 7/1082; A61G 7/1096; A61G 7/109; A61G 2210/10; A61G 13/123; A61G 13/125; A61G 2200/20; A61G 2200/327
USPC ... 5/621, 624, 648, 649, 600, 623, 632, 661, 5/619, 612; 128/845, 846, 878, 881, 882
See application file for complete search history.

(56) References Cited

U.S. PATENT DOCUMENTS

| | | | |
|---|---|---|---|
| 3,766,384 A | 10/1973 | Anderson | |
| 4,527,555 A * | 7/1985 | Ruf | A61B 6/505 5/600 |
| 4,872,656 A * | 10/1989 | Brendgord | A61G 13/0036 5/601 |
| 4,918,771 A * | 4/1990 | James | A61G 7/1017 5/87.1 |
| 5,056,635 A | 10/1991 | Bonnell | |
| 5,176,707 A * | 1/1993 | Phillips | A61H 1/008 602/34 |
| 5,239,716 A | 8/1993 | Fisk | |
| 5,372,147 A | 12/1994 | Lathrop, Jr. et al. | |
| 5,613,255 A | 3/1997 | Bish et al. | |
| 5,645,079 A * | 7/1997 | Zahiri | A61F 5/3769 128/882 |
| 5,658,315 A * | 8/1997 | Lamb | A61F 5/04 602/32 |
| 5,743,264 A | 4/1998 | Bonutti | |
| 5,806,117 A | 9/1998 | Gotfried | |
| 6,070,281 A | 6/2000 | Reich | |
| 6,085,749 A | 7/2000 | Wardle et al. | |
| 6,260,220 B1 | 7/2001 | Lamb et al. | |
| 6,286,164 B1 * | 9/2001 | Lamb | A61G 13/0036 128/845 |
| 6,375,355 B1 | 4/2002 | Fortin | |
| 6,643,873 B2 | 11/2003 | Heimbrock et al. | |
| 6,862,762 B1 | 3/2005 | Johnson et al. | |
| 7,246,390 B2 * | 7/2007 | Mitsuishi | A61H 1/0237 5/621 |
| 7,458,119 B2 | 12/2008 | Hornbach et al. | |
| 7,665,167 B2 * | 2/2010 | Branch | A61B 17/154 128/882 |
| 7,794,467 B2 | 9/2010 | McGinley et al. | |
| 8,707,476 B2 | 4/2014 | Sharps | |
| 8,991,230 B2 | 3/2015 | Jeong et al. | |
| 9,911,015 B2 | 3/2018 | Turnock et al. | |
| 9,920,218 B2 | 3/2018 | Liao et al. | |
| 9,961,224 B2 | 5/2018 | Utoh | |
| 2001/0015580 A1 * | 8/2001 | Sato | F15B 15/086 310/83 |
| 2004/0133983 A1 | 7/2004 | Newkirk et al. | |
| 2005/0268400 A1 | 12/2005 | Siccardi et al. | |
| 2007/0192960 A1 | 8/2007 | Jackson | |
| 2007/0251011 A1 | 11/2007 | Matta et al. | |
| 2008/0203249 A1 * | 8/2008 | Priest | A61F 5/3761 248/118 |
| 2010/0192300 A1 | 8/2010 | Tannoury et al. | |
| 2011/0099716 A1 | 5/2011 | Jackson | |
| 2011/0107516 A1 | 5/2011 | Jackson et al. | |
| 2012/0246829 A1 | 10/2012 | Lamb et al. | |
| 2012/0255122 A1 | 10/2012 | Diel et al. | |
| 2013/0133137 A1 | 5/2013 | Jackson et al. | |
| 2013/0219623 A1 | 8/2013 | Jackson | |

FOREIGN PATENT DOCUMENTS

| | | |
|---|---|---|
| FR | 2708195 A1 | 2/1995 |
| JP | 2005168881 A | 6/2005 |

* cited by examiner

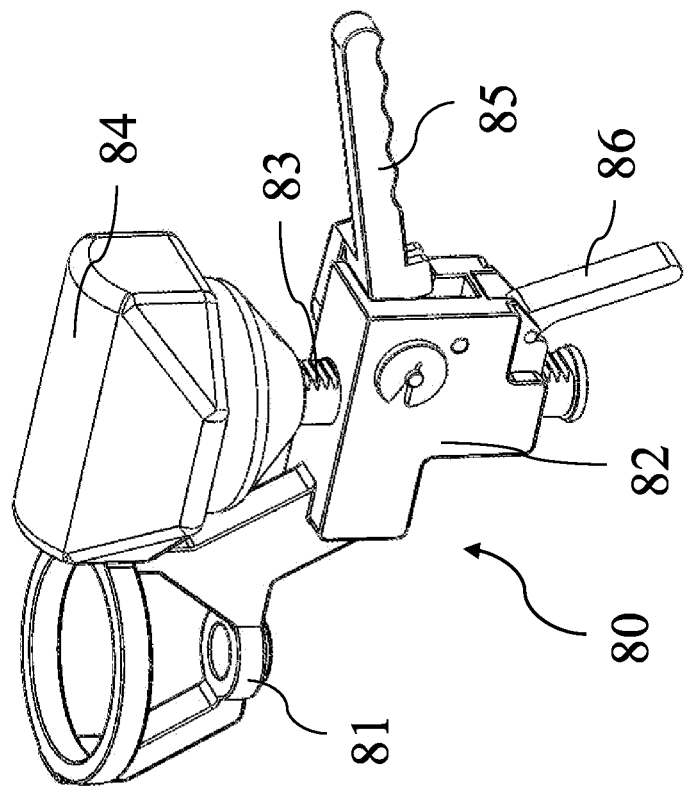
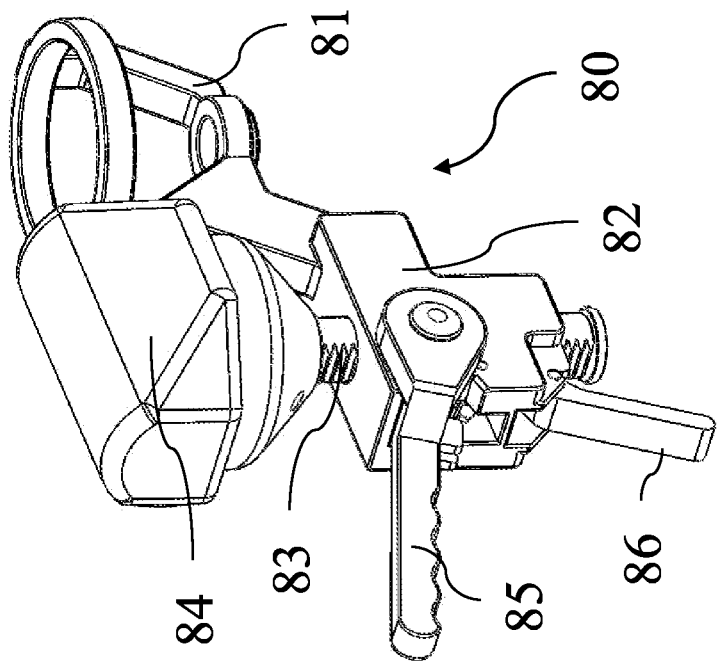
Fig. 14
Fig. 13

APPARATUS FOR POSITIONING THE LOWER LIMB OF A PATIENT DURING OPERATION, IN PARTICULAR FOR HIP REPLACEMENT OPERATIONS WITH ANTERIOR APPROACH, AND SURGICAL POSITIONING SYSTEM COMPRISING SAID APPARATUS

APPLICATION FIELD

The present invention applies to the orthopedic surgery sector, and in particular it refers to a positioning apparatus of the lower limb of a patient during operation, as well as an operation positioning system comprising said apparatus.

The apparatus can be usefully applied especially in the hip replacement operations with anterior approach.

PRIOR ART

The prior art offers several surgery techniques for the partial or total replacement of the hip prosthesis of a patient.

A recently introduced technique which is particularly appreciated due to its low invasiveness provides for an anterior approach which reaches the articulation of the hip passing through the intermuscular plane between the tensor of the fascia lata and the sartorius/rectus femoris muscle. The technique is known by the English acronym AMIS® (Anterior Minimally Invasive Surgery).

However, the correct execution of such technique requires a series of manipulation of the lower limb of the patient, so as to allow the surgeon to always operate in conditions of optimum access to the surgical site.

In this case, the limb of the patient positioned in the supine decubitus is first placed in slight traction so as to facilitate a first capsulotomy operation. The traction should then be slightly increased before the subsequent osteotomy operation of the femoral neck. Upon performing the osteotomy, there follows the application of a further traction and a subsequent external rotation of the articulation to allow the extraction of the severed head of the femur. Then, there follows the release of the traction on the limb before performing the milling of the acetabulum and positioning the replacement acetabulum. When preparing to introduce the femoral prosthesis, traction is applied once again, then there follows an external rotation exceeding 90°, the traction is released, the limb is hyper-extended and adducted. Then the limb is moved to its initial position before stitching.

As easily observable from the summarized description of the surgery technique provided above, the number and precision of the manipulations to be performed make it necessary to use an auxiliary apparatus for positioning the lower limb.

Though substantially meeting the needs of the industry, the positioning apparatuses known up to date show some unresolved drawbacks.

Firstly, it can be observed how such apparatuses should be maneuvered by a dedicated operator. Besides the surgeon and the surgery assistant, an additional person is therefore required in the operating theatre, with consequent increase of the intervention costs. Furthermore, the need to delegate to a third party the operations of moving the lower limb may lead to a complicating matter for the surgeon, who is forced to coordinate his intervention with that of another person.

Furthermore, it can be observed that most of the positioning apparatuses according to the prior art are not specifically designed for the previously described hip replacement technique; thus, the performances thereof are sometimes not optimal with reference to the technique in question.

Thus, the technical problem on which the present invention is based, is to provide a positioning apparatus capable of overcoming the drawbacks described in the prior art, and which can be particularly sufficiently maneuverable by the surgeon and particularly suitable for the AMIS® hip replacement technique.

SUMMARY OF THE INVENTION

The aforementioned technical problem is overcome, by a positioning apparatus of the lower limb of a patient during operation, comprising: at least a distal portion of a traction arm, which can be constrained to a connection member integral with a surgical table so as to define a traction axis of the lower limb of the patient; a support framework coupled to said distal portion so as to allow the adjustment of the position of one of its distal ends; a coupling constrained to said traction arm and arranged to be associated to the distal end of the lower limb of the patient; at least a first actuator which defines with its action a relative movement of the coupling with respect to the traction arm, at least a component of said relative movement being parallel to the traction axis.

The actuator is preferably an actuator cylinder of the pneumatic type, but it can also be an actuator cylinder of the hydraulic type or an electrical actuator or of any other type.

A man skilled in the art shall immediately observe how the previously described apparatus meets the needs of the surgeon in the hip replacement operations with anterior approach. In particular, it should be observed how the adjustment of the traction on the lower limb, which is absolutely required in the previously described AMIS® operating technique, can be easily operated through the aforementioned actuator.

In particular, an actuator cylinder of the pneumatic type can be easily and accurately controlled even remotely, and it can be easily integrated in an operating theatre where compressed air circuits are already provided for with wall-mounted power supply sockets.

The coupling is preferably supported by a first slider sliding along the traction arm, said first actuator determining the sliding of the first slider along the traction arm.

Such technical characteristic allows an accurate control of the traction direction of the limb, which shall coincide with the laying direction of the traction arm. In addition, it allows an extensive excursion of the first slider, i.e. a wide adjustment range for the degree of traction of the limb.

The first actuator is preferably a stem-less cylinder integrated in the traction arm, a piston within said first actuator cylinder being associated to the first slider. The connection between the first slider and the internal piston can for example be of the magnetic type.

Thanks to this solution, the longitudinal excursion of the slider is advantageously extended to the entire length of the cylinder, which may represent the entirety or a considerable portion of the traction arm.

At least the distal portion of said traction arm may actually be constituted by said first actuator cylinder, preferably accompanied by one or more guide stems of the first slider.

The support framework may comprise an upright to which there is slidably constrained a second slider, said second end of the traction arm being hinged to said second slider. A second actuator may thus be provided, adapted to determine the movement of the second slider along said upright.

Also in this case, the actuator is preferably an actuator cylinder of the pneumatic type, but it can also be an actuator cylinder of the hydraulic type or an electrical actuator or of any other type.

Also in this case, the actuator cylinder may be a stem-less cylinder which is vertically arranged adjacent to the upright of the support framework.

The second actuator advantageously allows automatically controlling the flexure and extension maneuvers of the lower limb of the patient.

The positioning apparatus may also comprise a rotary actuator intended to allow the relative rotation of the coupling with respect to the slider according to a rotation axis.

Such rotary actuator is preferably of the pneumatic type, but it may also be of the hydraulic type, electrical type or of any other type.

The rotary actuator advantageously allows automatically controlling the internal and external rotary maneuvers of the lower limb of the patient.

The positioning apparatus may advantageously comprise a control unit adapted to imparting controls to two or more of the previously mentioned actuators; preferably to the first actuator, to the second actuator and to the rotary actuator.

Such control unit may be moveable, interfaced to the support framework for example through flexible pipes (in cases where the actuators are of the pneumatic type). It can be positioned within the surgeon's reach, who is thus capable of personally maneuvering the positioning apparatus.

The control unit may in particular comprise a pedal interface, so that the surgeon can manoeuvre the positioning apparatus even with busy hands.

The support framework of the apparatus may comprise a wheel-equipped carriage with fixed wheels facing directions parallel to each other; said support framework further comprising at least one support wheel which can be directed in the offset direction with respect to the fixed wheels.

The framework may thus move in one sole direction (for example moving away/approaching with respect to the operating table) when the support wheel is retracted; while upon the extraction of the latter it shall be possible to perform lateral movements required for the correct positioning of the limb of the patient.

The technical problem is moreover overcome by a surgical positioning system comprising a positioning apparatus according to what has been described previously and an adapter plane predisposed for covering a surgical table, and coupled to the positioning apparatus through a connection member; said connection member defining a proximal portion of the traction arm misaligned with respect to the distal portion.

Thanks to this misalignment it is possible to recover the angular offset which would have otherwise been created between the distal portion of the traction arm and the leg of the patient.

Further characteristics and advantages shall be more evident from the detailed description hereinafter of two preferred non-exclusive embodiments of the present invention, with reference to the attached figures provided by way of non-limiting example.

BRIEF DESCRIPTION OF THE DRAWINGS

FIG. 13 represents a perspective view of a second construction detail of the adapter plane of FIG. 7;

FIG. 14 represents another perspective view of the second construction detail of FIG. 13.

DETAILED DESCRIPTION

Figure 1:
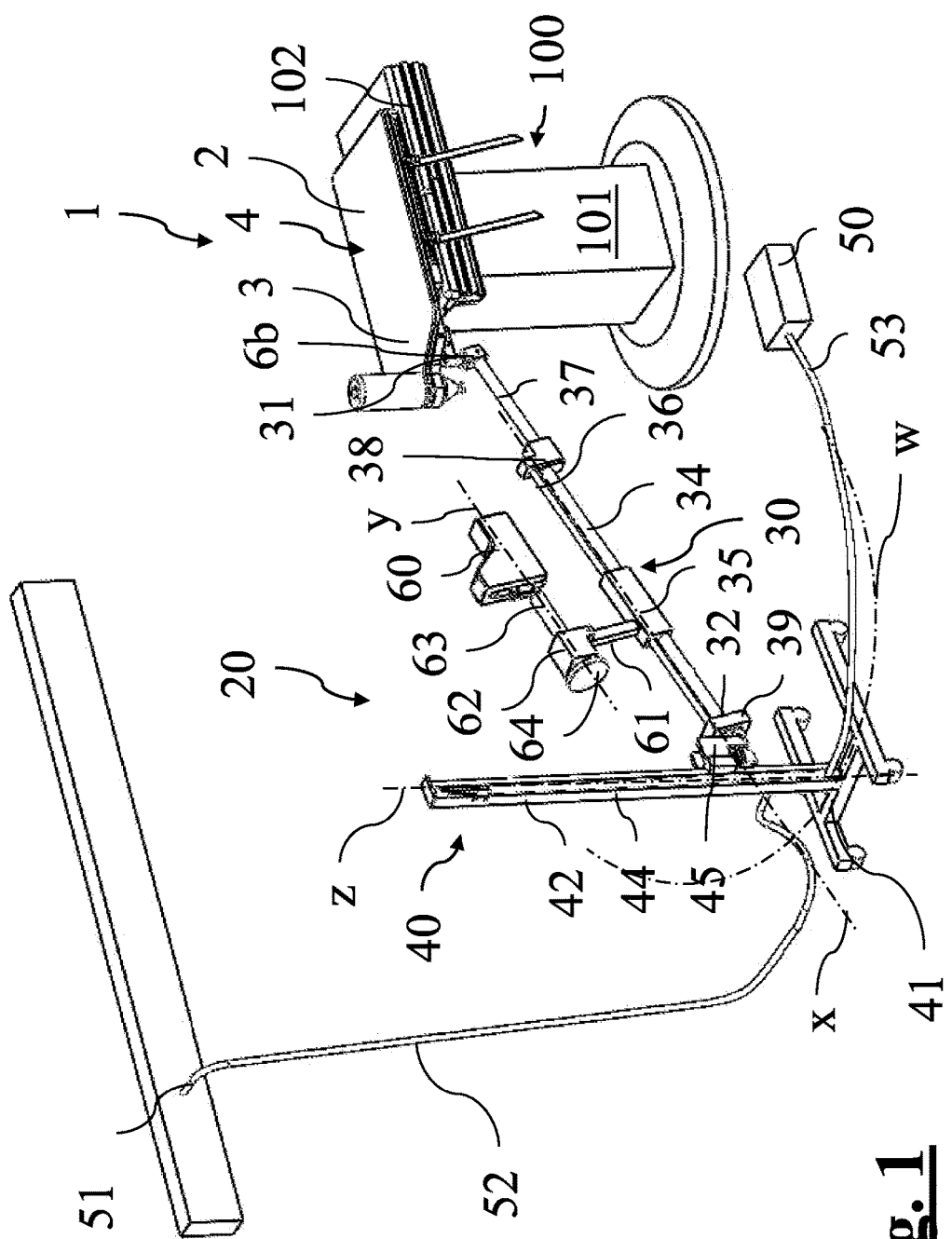
FIG. 1 represents a perspective view of a positioning apparatus of the lower limb of a patient according to a first embodiment of the invention, associated to a surgical table with adapter plane.
Figure 2:
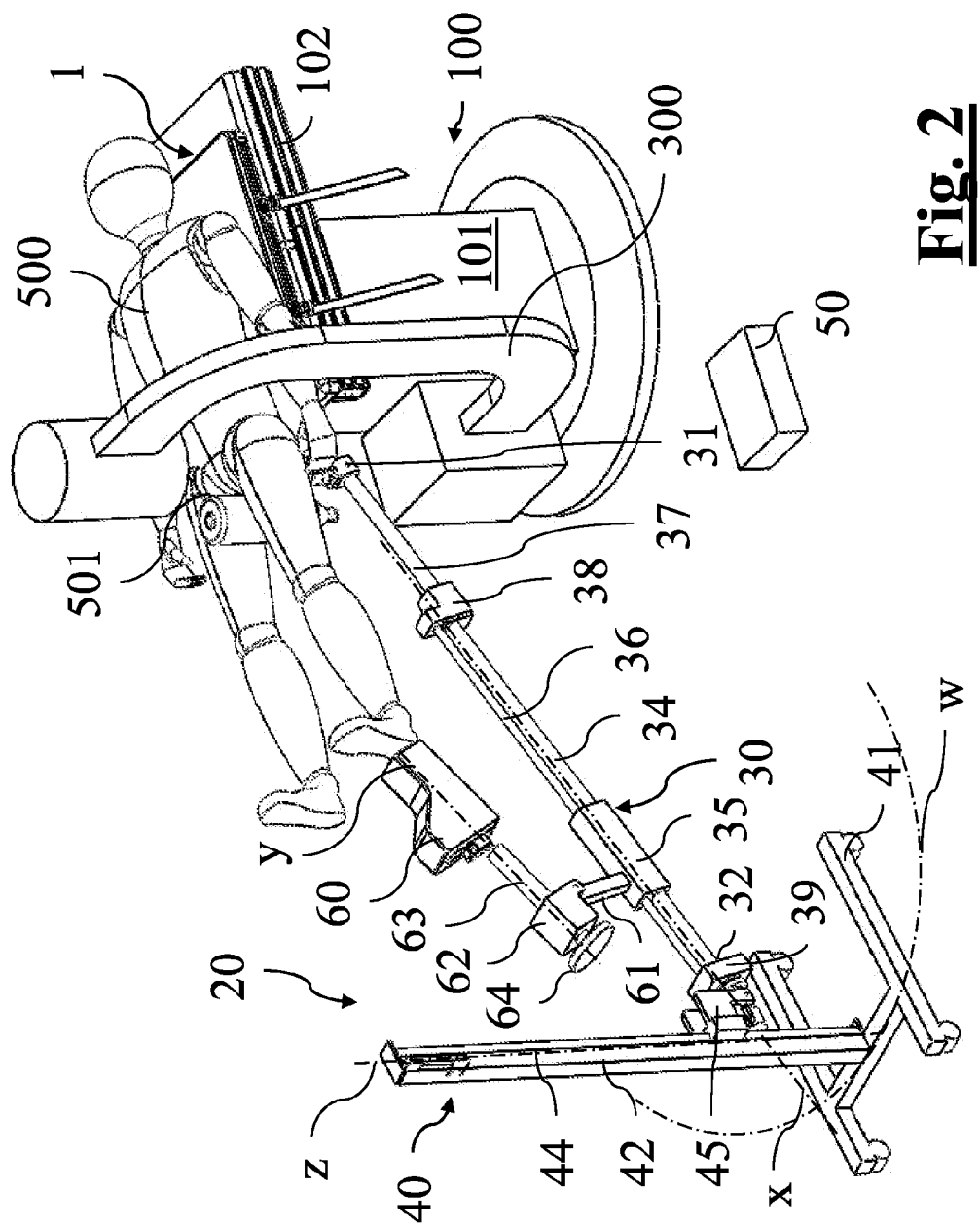
FIG. 2 represents a perspective view of the system of FIG. 1, during an hip replacement operation with anterior approach.

With reference to FIGS. 1-6 attached is identified an operation positioning system comprising: a positioning apparatus 20 of the lower limb of the patient 500 according to a first embodiment of the present invention; and an adapter plane 1 associated thereto.

The adapter plane 1 is rigidly coupled over a surgical table 100. For the sake of completeness and for a better understanding of the invention, a summarized description of such devices is provided hereinafter.

The surgical table 100 comprises a central column 101 which holds a support plane 102, which is made of radiopaque material, such as for example metal material.

The adapter plane 1 comprises a main portion 2 overlapping the support plane 102 of the surgical table. The main portion 2 has a substantially rectangular development with width equivalent to that of the support plane 102 which is partially covered thereby. Thus, the main portion 2 has two parallel sides 2a substantially aligned to the perimeter of the support plane 102 and a bottom side 2b misaligned with respect to such perimeter.

The adapter plane 1 further comprises a secondary portion 3 planarly contiguous to the main one, but which extends beyond the perimeter of the underlying support plane 102. Thus, such secondary portion 3 develops projecting laterally with respect to the surgical table 100 which supports the adapter plane 1.

A radiographic apparatus 300 (preferably a fluoroscope) with a C-shaped arm, integral with the surgical table 100, is arranged astride the secondary portion 3 of the adapter plane 1.

The secondary portion 3 of the adapter plane is substantially shaped to form an isosceles triangle, i.e. it has two converging sides 3a which, starting from the parallel sides 2a of the main portion, converge towards an end point 3b arranged along a median longitudinal axis m of the adapter plane 1.

The two converging sides 3a are inclined with respect to the median longitudinal axis m by an angle comprised between 45° and 75°, in particular 60°.

At the end point 3b the adapter plane comprises a perineal support 5. The perineal support 5 is a vertical sleeve, which rises from the support surface 4 and is located in an anterior position—i.e. further overhanging—with respect to the part of the plane defined by the converging sides 3a. The perineal support 5 is advantageously defined by a rigid vertical pin 5a surrounded by a padding 5b.

The lower face of the secondary portion 3 has a conical appendix 8, which is coaxial and opposite to the perineal support 5. The conical appendix 8 ends with an enlarged-head cylinder. Such conical appendix 8 allows the coupling of a thigh hoisting device 80, singularly observable in FIGS. 13-14, whose characteristics and functions are described in detail hereinafter.

Still on the lower face of the secondary portion 3, along the median longitudinal axis m but in a position closer to the perimeter of the support plane 102, there is extended a connection member 6 for associating the positioning apparatus 20 of the lower limb of the patient 500.

Such connection member 6 comprises a vertical appendix 6a rotatably associated below the secondary portion 3, such vertical appendix laterally has a hinge 6b to which there can be associated a member for coupling the positioning apparatus 20.

It should be observed that the main portion 2 and the secondary portion 3 described previously have a uniform structure, and they are both made of the same radiotransparent material, in particular carbon fibre.

The uniform structure of the two portions 2, 3 is divided into two functionally distinct overlapping layers; a lower layer 9a represents the actual support structure, while an upper layer 9b stands for a comfort padding.

On the lower layer 9a, in particular along the parallel sides 2a of the main portion 2, there are extended two lateral tracks 7a. To each track there are associated two slidable slides 7b which carry retention means for an equivalent number of belts 7, which allow the quick fixing of the adapter plane to the underlying surgical table.

Now, following is the description of the actual positioning apparatus 20.

The positioning apparatus 20 comprises a traction arm 30 defining a traction axis x. A proximal end 31 of such traction arm 30 is hinged to the hinge 6b of the previously described adapter plane 1. The distal end 32 is instead hinged to a framework 40 for supporting the positioning apparatus 20 as described below.

The traction arm 30 comprises a proximal portion 37, defined by a rigid bar, on the proximal end side 31; and a distal portion 34, 36, on the distal end side 32.

The distal portion 34, 36 is made up of a first actuator cylinder 34 arranged adjacent to a guide stem 36 parallel thereto; the two elements connect a proximal fitting 38, integral with the rigid bar of the proximal portion 37, to a distal fitting 39, hinged to the support framework 40.

The first actuator cylinder 34 is a double acting pneumatic cylinder of the stem-less type, i.e. internally comprising a piston without a thrust stem. The internal piston is instead magnetically associated to a first slider 35, which embraces both the first actuator cylinder 34 and the guide stem 36 and is slidable along the latter in the direction of the traction axis x. Thus, actuating the first actuation cylinder 34 allows to determine a stroke of the first slider 35 along the traction arm 30.

The first slider 35 carries a rigid rod 61, which extends orthogonally upwards with respect to the traction arm 30. At the end of such rigid rod 61 there is provided a connection member 62, which connects it to a support shaft 63 at the end of which there is integrally associated a coupling 60 for the distal end of the lower limb of the patient. The coupling 60 is particularly provided in form of a traction shoe of the known type. The connection member 62 allows to vary the angle between the rigid rod 61 and the support shaft 63.

The support shaft 63 defines a rotation axis y of the traction shoe. Within the connection member 62 there is present a rotary actuator of the pneumatic type, which allows to rotate the support shaft 63 and the traction shoe associated thereto around said rotation axis y. An emergency flywheel 64 is provided for the rotation thereof should the pneumatic system fail (for example due to power failure).

The support framework 40 is mounted on a wheel-equipped carriage 41 slidable on the floor of the operating theatre.

Such wheel-equipped carriage 41 has a H-shaped horizontal structure H, from the centre of which there rises an upright 42 extended vertically according to an extension axis z.

Adjacent to the upright, 42 there is arranged a second actuator cylinder 44. This cylinder also is a double-acting pneumatic cylinder of the stem-less type, magnetically associated to a second slider 45. Thus, the second slider may be controlled sliding along the extension axis z.

The second slider 45 is hinged to the distal fitting 39 of the traction arm 30. It should be observed that there are provided means for locking the slider 45, such as a mechanical lock, configured for automatically locking such slider 45 at the end of the translation set by the actuator 44. Such mechanical lock maintains the position of the second slider 45 even if the pneumatic system fails (for example in case of power failure).

Analogous locking means are also provided for the slider 35 and configured, just like for the slider 45, for providing a stop brake and a safety lock.

Since such locking means are of the per-se known type, they are not represented for the sake of description simplicity.

Furthermore, at the lower end of the support framework 40 there are provided one or more support wheels, which can be control-extracted when the second slider 45 is at a lower end-stroke position. Such support wheels allow in case of need the sliding of the wheel-equipped carriage 41 in the lateral direction. Indeed, it shall be observed that the fixed wheels of the carriage are locked in the direction of the patient, so that the carriage cannot move in the lateral direction; the support wheel is instead mounted orthogonally to the others, so as to allow the lateral movement when extracted.

The positioning apparatus 20 provides for a pneumatic system which connects the first actuator cylinder 34, the second actuator cylinder 44 and the rotary actuator. The system may be suitably connected, through an inlet connection 52, to a wall-mounted socket 51 of a compressed air distribution system. The system further comprises a control unit 50, which is connected to the support framework 40 by means of a flexible connection 53. The control unit 50 consists in a control box provided with a pedal interface, so as to be actuated by the surgeon during the operation.

The positioning apparatus 20 allows to perform different movements on the lower limb of the patient connected thereto through the traction shoe.

By actuating the rotary actuator there is obtained a rotation of the traction shoe around the rotation axis y, thus leading to an internal or external rotation of the limb.

The first actuator cylinder 34 allows to translate the traction shoe along the traction axis x, thus defining a traction of the limb or a release of such traction.

The second actuator cylinder 44 allows to lift or to low the second end 32 of the traction arm 30 along the extension axis z, respectively determining a flexure or an extension of the limb.

Lastly, after extracting the previously described support wheel, the wheel-equipped carriage 41 can be translated according to a circle arc w, defined by the hinging of the first end 31 of the traction arm. Such displacement defines the adduction/abduction movements of the lower limb of the patient.

Figure 3:
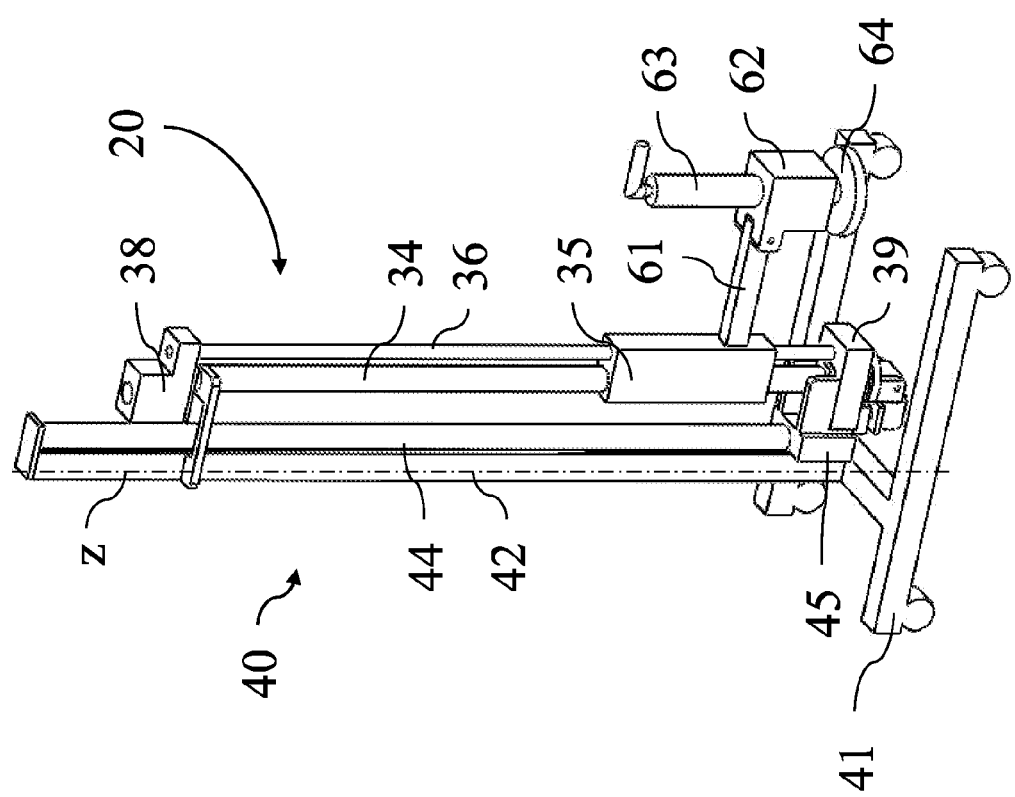
FIG. 3 represents a perspective view of the positioning apparatus observable in FIG. 1, in folded configuration.
Figure 4:
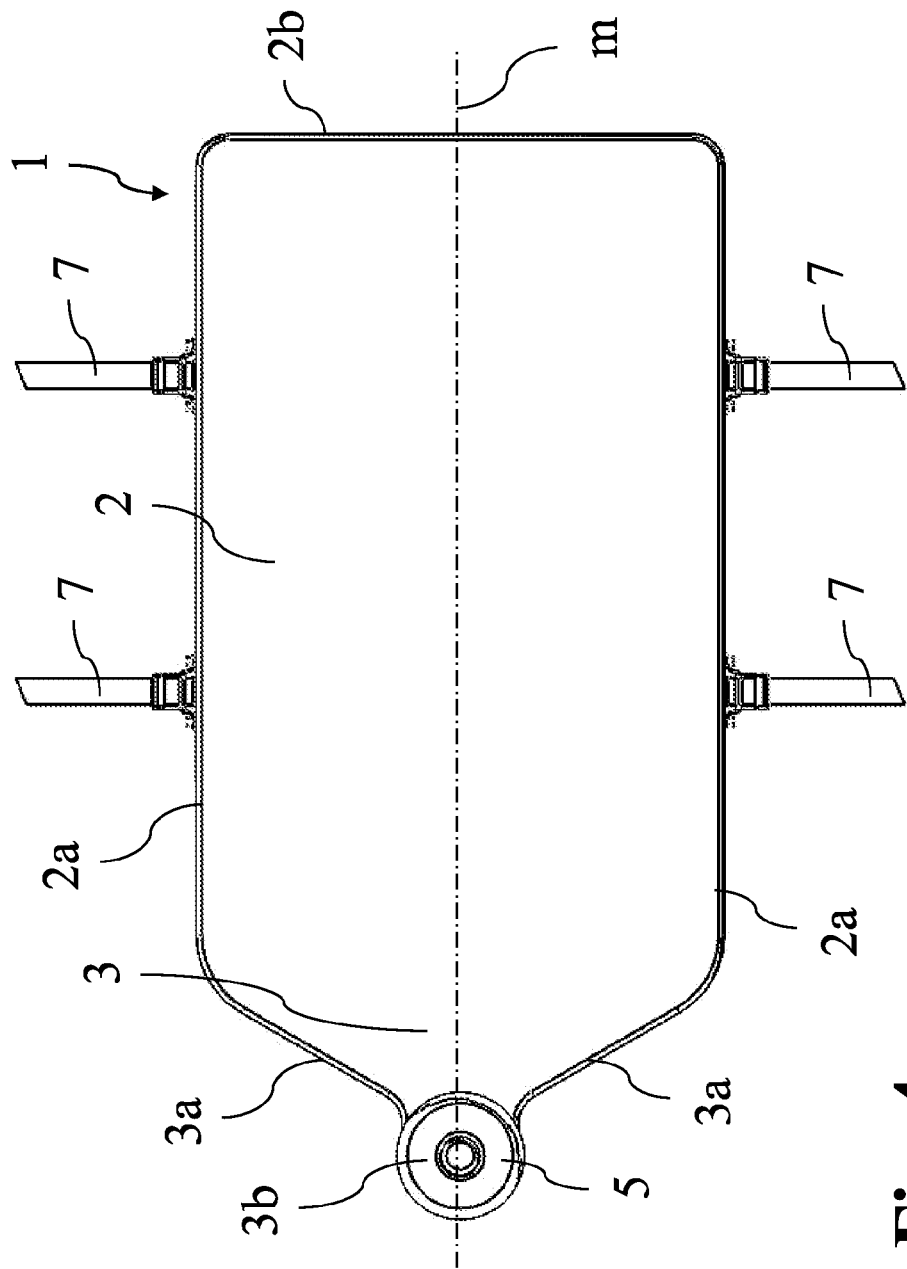
FIG. 4 represents a top orthogonal view of the adapter plane of FIG. 1.
Figure 5:
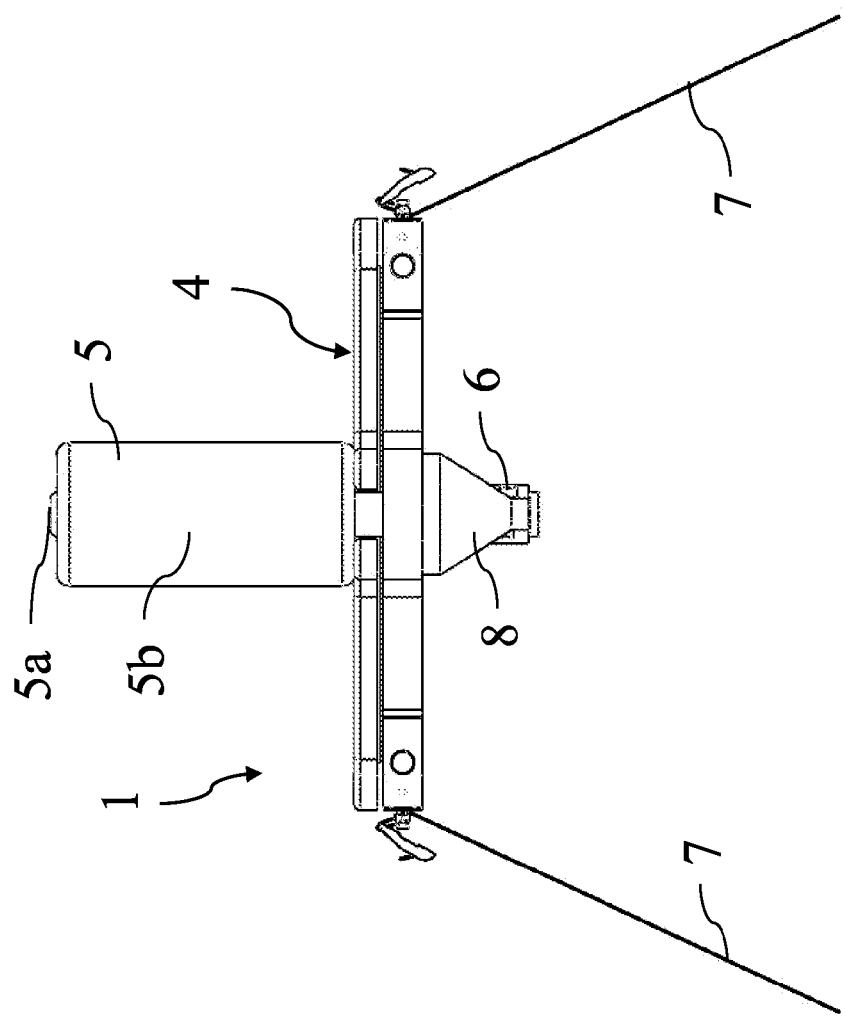
FIG. 5 represents a front orthogonal view of the adapter plane of FIG. 1.
Figure 6:
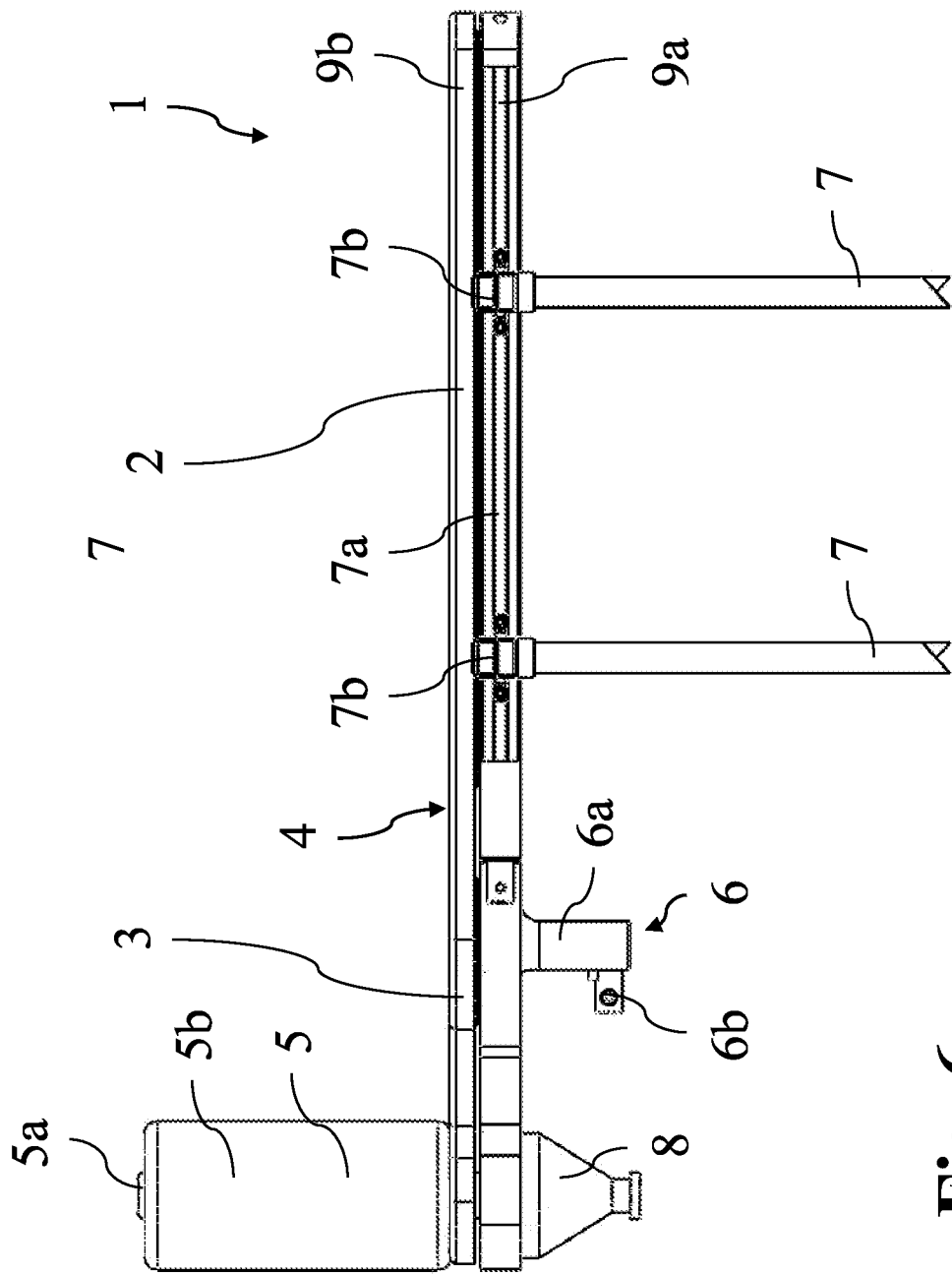
FIG. 6 represents a lateral orthogonal view of the adapter plane of FIG. 1.

It should be observed that the traction arm 30 may be folded against the upright 42 of the support framework 40 with the aim of putting the apparatus away when not used, as illustrated in FIG. 3. It should be observed that in such case the rod 61 is rotated by 180° moving it towards the external of the traction arm 30.

With reference to the attached FIGS. 7-12 there is identified an improved embodiment of the surgical positioning system addressed previously.

The improved surgical positioning system has a second embodiment of the apparatus 20' for positioning the lower limb 500 according to the present invention, and an adapter plane 1' associated thereto.

For the sake of completeness and for a better understanding of the invention, in this second embodiment of the invention a summarized description of the adapter plane 1' is provided hereinafter.

Such second embodiment of the adapter plane 1' is in particular illustrated in FIGS. 9-12, where portions identical or analogous to those described previously according to the first embodiment are identified with the same reference numbers by the symbol of the first.

The second embodiment of the adapter plane 1' is substantially equal to the first embodiment, being different only with respect to the configuration of the connection member 6' which is intended for coupling with the positioning apparatus 20' of the lower limb of the patient 500.

Figure 12:
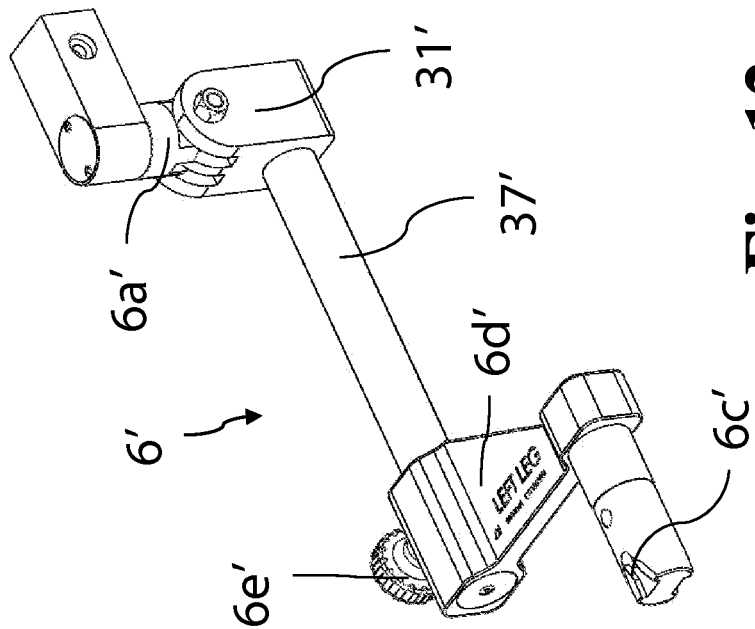
FIG. 12 represents a perspective view of the construction detail of FIG. 11, in a second configuration.
Figure 11:
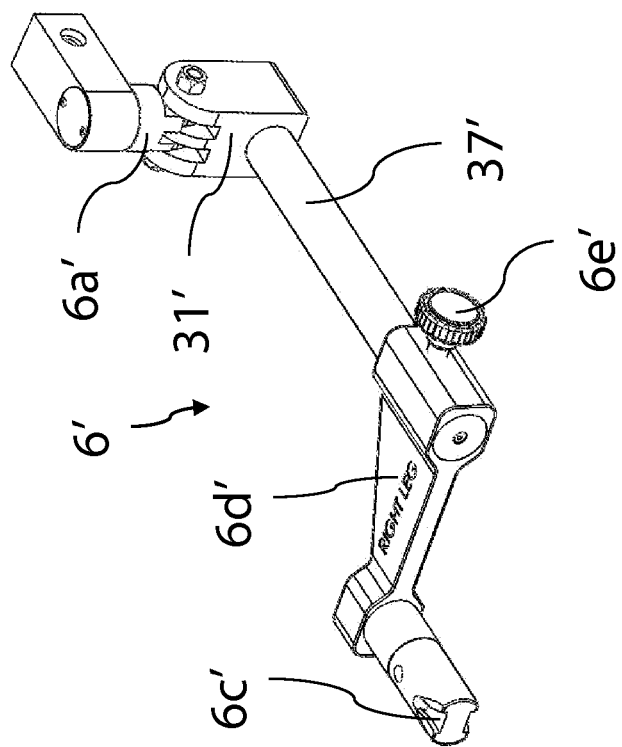
FIG. 11 represents a perspective view of a first construction detail of the adapter plane of FIG. 7, in a first configuration.

In this improved embodiment, which is illustrated in detail in in FIGS. 11 and 12, the connection member 6' already comprises a proximal portion 37' of the traction arm 30'. The distal portion 34', 36' of such traction arm 30' remains instead part of the positioning apparatus and is connected to the previous portion by means of a linear joint $6c'$.

The connection member 6' comprises in particular a vertical appendix $6a'$ which extends below the secondary portion 3' of the adapter plane 1'. The vertical appendix $6a'$ is rotatably articulated with respect to the above laying plane according to a vertical axis.

Below the vertical appendix $6a'$ there is hinged, according to a horizontal axis, a proximal end 31' of the proximal portion 37' of the traction arm 30' mentioned previously, which consists in a rigid bar.

At the distal end of the rigid bar there is associated a spacer element $6d'$ which connects the proximal portion 37' to the linear joint $6c'$. The spacer element $6d'$ develops transverse with respect to the parallel axis of the proximal portion 37' and of the linear joint $6c'$; in particular its dimension is such to allow the positioning of the linear joint $6c'$ beneath the lower limb of the patient 500, so as to align the traction arm 30' therewith.

It should be observed that a spacer element $6d'$ comprises a knob $6e'$ which allows to unlock the element to perform a 180° rotation around the axis of the proximal portion 37', so as to be able to adjust the configuration of the connection member 6' according to the limb to be operated.

The entire connection member 6' described above is preferably made of radiotransparent material.

The connection member 6' in its improved embodiment shows several advantages with respect to the connection member 6 of the first embodiment described previously.

Firstly, the connection to the positioning apparatus is performed through a linear joint, and no longer at the point of articulation of the traction arm. This allows to simplify the operations of connecting the positioning apparatus and to reduce the stress on the joint, which is a potential breakage point.

Furthermore, the spacing element allows the misalignment of the two portions of the traction arm, thus allowing a perfect alignment of the distal portion with the lower limb of the patient and considerably improving the precision of the manipulations carried out through the positioning apparatus.

Lastly, the structural division of the device below the spacer element allows the entire portion of the device, which falls within the field of action of the fluoroscope during the surgical intervention, to be made of radiotransparent material.

Now, following is the description of the second embodiment of the actual positioning apparatus 20'.

Figure 7:
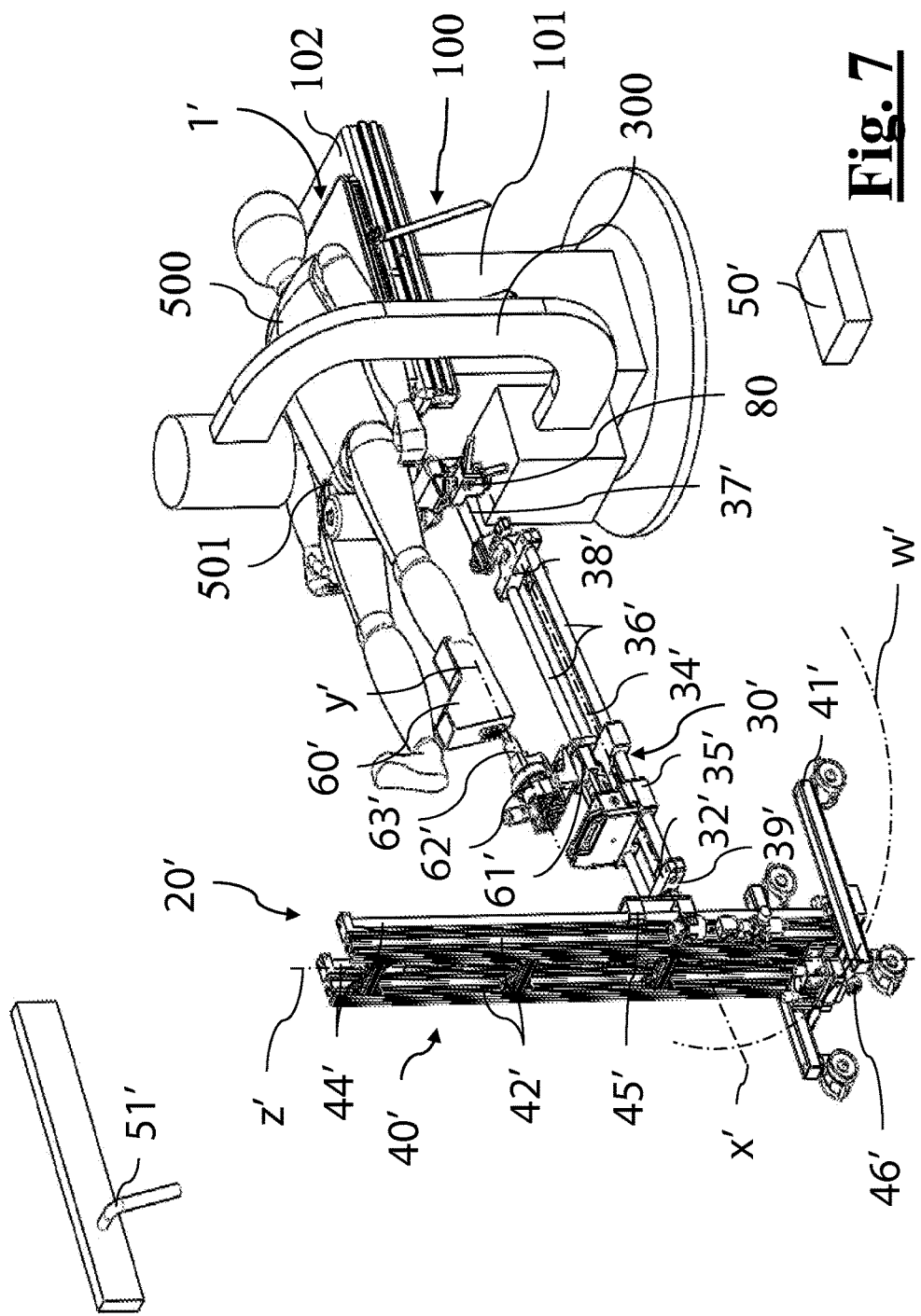
FIG. 7 represents a perspective view of a positioning apparatus of the lower limb of a patient according to an alternative embodiment of the invention, associated to a surgical table with adapter plane.
Figure 8:
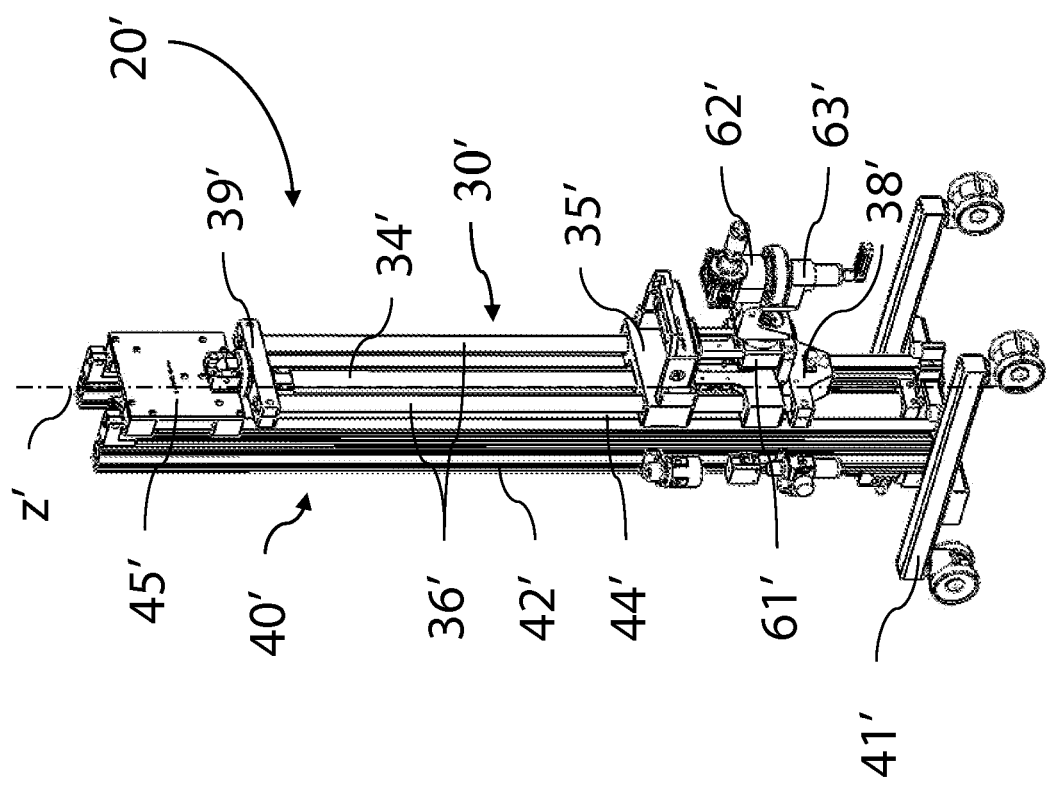
FIG. 8 represents a perspective view of the positioning apparatus observable in FIG. 7, in folded configuration.
Figure 9:
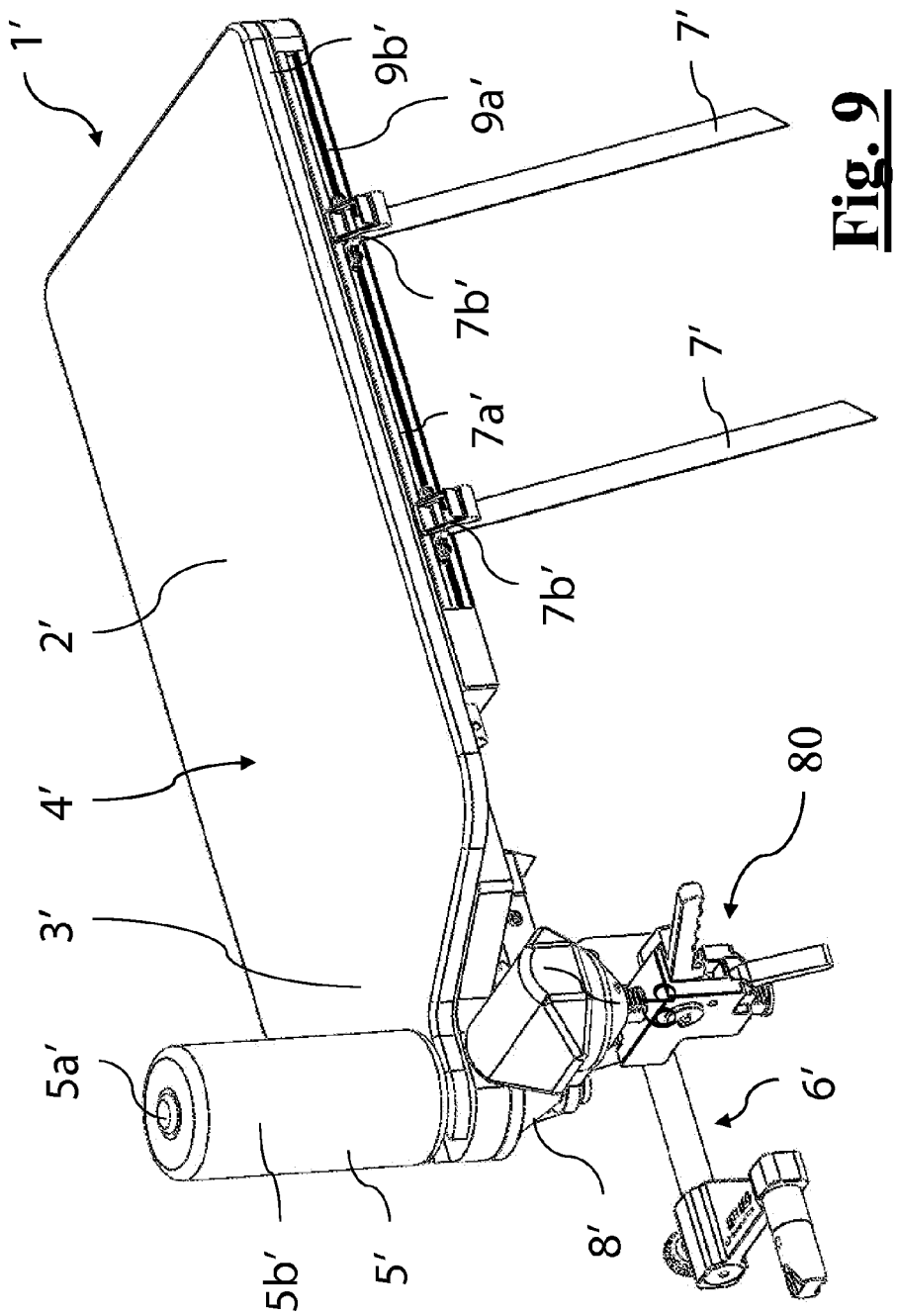
FIG. 9 represents a perspective view of the adapter plane of FIG. 7.
Figure 10:
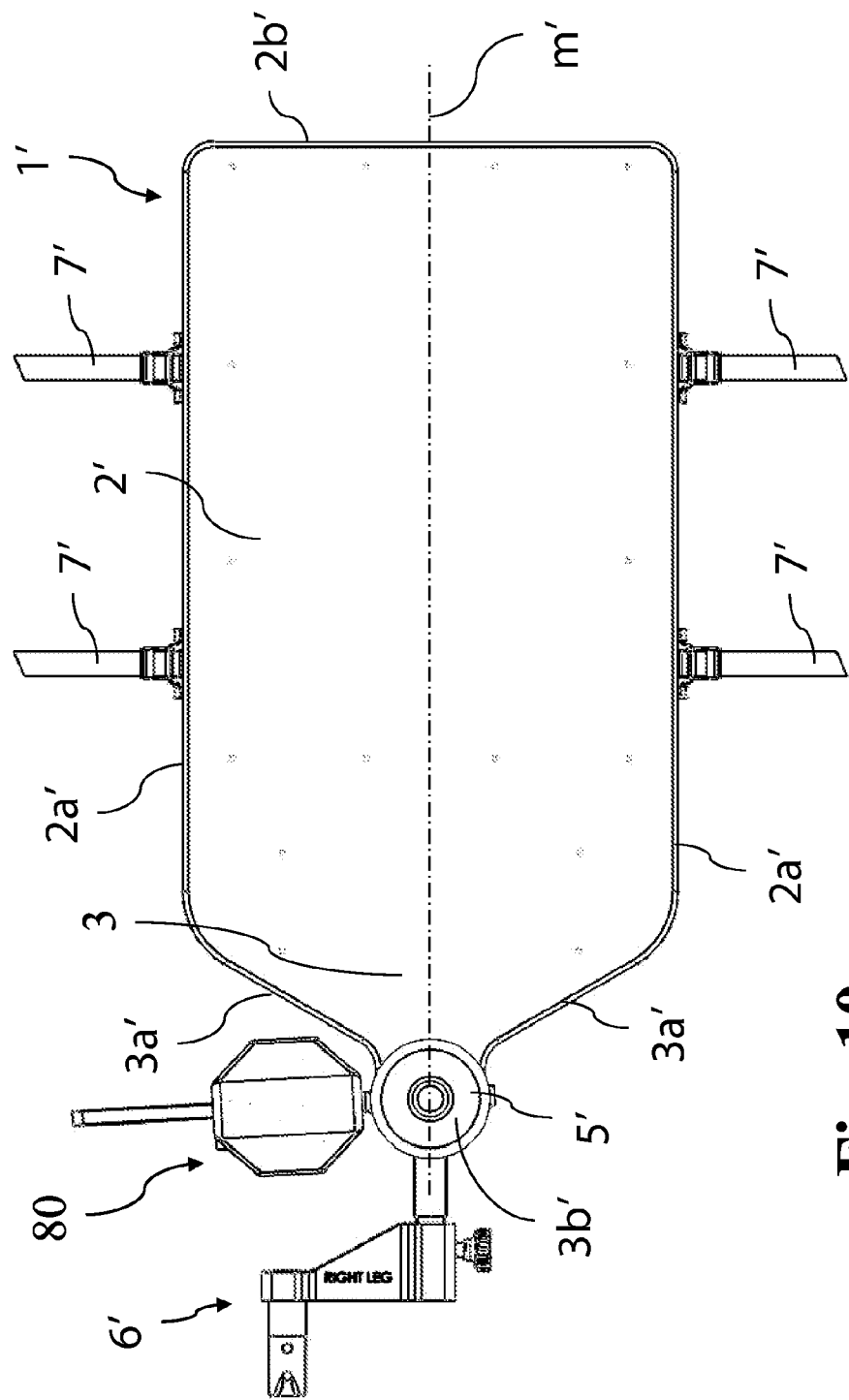
FIG. 10 represents a top view of the adapter plane of FIG. 7.

The second embodiment of the positioning apparatus 20' is in particular illustrated in FIGS. 7 and 8, where portions identical or analogous to those described previously regarding the first embodiment are identified with the same reference numbers by the symbol of the first.

Once again, reference shall be made to the previous description for the description of the parts of the device substantially analogous to the first embodiment, while the description that follows only identifies the different aspects of the second embodiment.

Firstly, it should be observed how the traction arm 30' is now partly defined by the connection member 6' of the adapter plane 1', while the sole distal portion 34', 36' is part of the positioning apparatus 20'. In particular, it is this distal portion 34', 36', misaligned with respect to the proximal portion 37', that defines the traction axis x' parallel to the lower limb of the patient 500.

The distal portion 34', 36' itself has a different structure: it comprises two parallel guide stems 36' which connect the distal fitting 39' with the proximal fitting 38'; the latter is predisposed for mating with the previously mentioned linear joint $6c'$.

The first actuator cylinder 34', still constituted by a double acting pneumatic cylinder of the stem-less type, is arranged between the two guide stems 36', in a slightly lowered position with respect thereto.

The first slider 35' embraces both guide stems 36' and the first actuator cylinder 34' interposed thereto.

The first slider 35' no longer carries a rigid rod, which has been replaced by an adjustable slide 61' according to the traction axis x' over which there is provided the adjustable connection member 62', provided as before with the support shaft 63' and the relative shoe coupling 60'.

The structure of the support framework 40' is substantially analogous to that of the previously described embodiment, excluding the doubling of the upright/actuator unit 42', 44' so as to provide greater mechanical resistance to the entirety.

Furthermore, it should be observed that in FIG. 7 there can be observed a concealable support wheel 46' which allows the lateral movement of the support framework 40'; the representation of such element was omitted in the drawings regarding the first embodiment for the sake of clearness.

Furthermore, it should be observed that the pneumatic system of the second embodiment is substantially analogous to that of the first embodiment; the wall socket 51' and control unit 50' connections to the support framework 40' were omitted in FIG. 7 for the sake of clearness.

Lastly, it should be observed that, with reference to the second embodiment described previously, the folding position provides for the positioning of the second slider 45' in the upper end-stroke position and the subsequent folding of the traction arm 30' downwards along the column of the support framework 40'. Such folding method, represented in FIG. 8, does not provided for the 180° rotation of the connection member 62'.

Even in this second embodiment of the invention there are provided means for locking the sliders 35' 45' configured for automatically locking the sliders 35' 45' at the end of the translation set by the actuators 34' 44'. Such locking means serve both as stop brakes and safety lock in case of malfunction of the pneumatic system (for example due to power failure).

The invention also innovatively provides for the presence of means for releasing the first slider 35; 35' configured for automatically unlocking such first slider 35; 35' during the translation of the second translating slider 45; 45'.

Thus, every time there is performed the extension or flexure movement of the leg (lowering and lifting the leg) through the actuator 44, 44', the mechanical lock of the traction arm is unlocked, freeing the movement of the slider 35, 35' and allowing the automatic release of the traction. This prevents the muscles of the leg from being subjected to further traction, thus avoiding possible muscle lesions and in any case post operative pains for the patient.

Obviously, it is provided that such automatic release of the traction can be performed in case of emergency. Actually, in such situation, all movements are performed manually to allow completing the intervention. Hence, it is firstly necessary to introduce the traction by manually unlocking the mechanical lock and subsequently performing the flexure or extension movement.

The actuators 34, 44; 34', 44', the means for locking the sliders 35; 35';45; 45' and the means for releasing said first translating slider 35; 35' are each controlled by the control unit 50, 50'.

Lastly, there is described the thigh hoisting device 80, couplable to the conical appendix 8; 8' of the adapter plane 1; 1' in both embodiments thereof.

The thigh hoister 80, singularly observable in FIGS. 13-14, comprises a main body 82 from which there departs a cup-like coupling appendix 81 couplable to the conical appendix 8, 8'. The defined coupling is of the rotatable type, so that the thigh hoister 80 can be easily moved rightwards or leftwards with respect to the end 3b, 3b' depending on the limb to be operated.

The main body 82 houses a mounted rack rod 83 movable vertically which carries at the top part a cushion 84 for supporting the thigh of the patient.

The thigh hoister 80 provides for an actuation lever 85, which cooperates with the rack rod 83 thus determining a predefined hoisting of the support cushion 84 upon each traction. The movement of the rack rod 83 in the opposite direction is prevented by a proper beak integral with the end of a release lever 86; when the release lever 86 is actuated, the beak no longer exerts the locking action thereof and the support cushion 84 lowers due to gravity.

The thigh hoister is made of plastic material or however radiotransparent material so as not to interfere with the operation of the fluoroscope.

Obviously, the described invention may be subjected, by a man skilled in the art with the aim of meeting contingent and specific requirements, to various modifications and variants all falling within the scope of protection of the invention as defined by the following claims.

The invention claimed is:

1. A positioning apparatus for positioning a lower limb of a patient during an operation on a surgical table, the positioning apparatus comprising:
   a traction arm comprising a distal portion being constrained by a connection member integral with the surgical table so as to define an axis for traction of the lower limb of the patient;
   a support framework coupled to said distal portion so as to allow adjustment of a distal end of said support framework;
   a coupling constrained to said traction arm and arranged to be associated to a distal end of the lower limb of the patient;
   at least one first actuator configured to control relative movement of said coupling with respect to said traction arm, at least one component of the relative movement being parallel to the axis for the traction;
   a first slider being slidable along said traction arm;
   a first shaft extending from said first slider and transverse to said traction arm;
   a rotary connector coupled to said first shaft;
   a second shaft having a first end coupled to said rotary connector, and a second end opposite said first end coupled to said coupling, said second shaft extending parallel to said traction arm; and
   a flywheel coupled to said rotary connector and configured to permit manual rotation of said second shaft; and
   a rotary actuator coupled to said first shaft and configured to rotate said second shaft;
   said at least one first actuator configured to determine sliding of said first slider along said traction arm;
   said support framework comprising
      a second slider,
      an upright to which there is slidably constrained said second slider,
      said distal portion of the traction arm being hinged to said second slider,
      a second actuator configured to determine movement of said second slider along said upright,
      a carriage,
      a plurality of wheels coupled to said carriage and facing directions parallel to each other,
      at least one support wheel configured to be directed in an offset direction with respect to said plurality of wheels,
      a plurality of locking devices configured to lock said first and second sliders, and automatically lock said first and second sliders at an end of movement set by said at least one first actuator and said second actuator, and
      a release device configured to release said first slider automatically during movement of said second slider;

said traction arm being configured to switch between a first folded state and a second extended state, the first folded state having said traction arm folded so that said distal portion of said traction arm is adjacent said upright.

2. The positioning apparatus according to claim 1, wherein said at least one first actuator comprises a stem-less actuator cylinder integrated in said traction arm, and a piston internal to said stem-less actuator cylinder being associated to said first slider.

3. The positioning apparatus according to claim 1, further comprising a control unit configured to control said at least one first actuator and said second actuator, and a respective locking device associated with said first slider.

4. The positioning apparatus according to claim 3, wherein each actuator comprises a pneumatic type actuator.

5. A surgical positioning system comprising:
a surgical table;
a connection member integrated with said surgical table;
a positioning apparatus for positioning a lower limb of a patient during an operation, the positioning apparatus comprising
a traction arm comprising a distal portion being constrained by said connection member so as to define an axis for traction of the lower limb of the patient,
a support framework coupled to said distal portion so as to allow adjustment of a distal end of said support framework,
a coupling constrained to said traction arm and arranged to be associated to a distal end of the lower limb of the patient,
at least one first actuator configured to control relative movement of said coupling with respect to said traction arm, at least one component of the relative movement being parallel to the axis for the traction,
a first slider being slidable along said traction arm,
a first shaft extending from said first slider and transverse to said traction arm,
a rotary connector coupled to said first shaft,
a second shaft having a first end coupled to said rotary connector, and a second end opposite said first end coupled to said coupling, said second shaft extending parallel to said traction arm,
a flywheel coupled to said rotary connector and configured to permit manual rotation of said second shaft, and
a rotary actuator coupled to said first shaft and configured to rotate said second shaft,
said at least one first actuator configured to determine sliding of said first slider along said traction arm,
said support framework comprising
a second slider,
an upright to which there is slidably constrained said second slider,
said distal portion of the traction arm being hinged to said second slider,
a second actuator configured to determine movement of said second slider along said upright,
a carriage,
a plurality of wheels coupled to said carriage and facing directions parallel to each other,
at least one support wheel configured to be directed in an offset direction with respect to said plurality of wheels,
a plurality of locking devices configured to
lock said first and second sliders, and
automatically lock said first and second sliders at an end of movement set by said at least one first actuator and said second actuator, and a release device configured to release said first slider automatically during movement of said second slider,
said traction arm being configured to switch between a first folded state and a second extended state, the first folded state having said traction arm folded so that said distal portion of said traction arm is adjacent said upright;
and
an adapter plane configured to cover said surgical table, and coupled to said positioning apparatus through said connection member;
said connection member defining a proximal portion of said traction arm misaligned with respect to said distal portion.

6. The surgical positioning system according to claim 5, wherein said at least one first actuator comprises a stem-less actuator cylinder integrated in said traction arm, and a piston internal to said stem-less actuator cylinder being associated to said first slider.

7. The surgical positioning system according to claim 5, further comprising a control unit configured to control said at least one first actuator and said second actuator, and a respective locking device associated with said first slider.

8. The surgical positioning system according to claim 7, wherein each actuator comprises a pneumatic type actuator.

* * * * *